United States Patent [19]
Eibl et al.

[11] Patent Number: 6,017,891
[45] Date of Patent: *Jan. 25, 2000

[54] STABLE PREPARATION FOR THE TREATMENT OF BLOOD COAGULATION DISORDERS

[75] Inventors: Johann Eibl; Hans Peter Schwarz; Juergen Siekmann; Peter Turecek, all of Vienna, Austria

[73] Assignee: Baxter Aktiengesellschaft, Vienna, Austria

[*] Notice: This patent is subject to a terminal disclaimer.

[21] Appl. No.: 08/924,533

[22] Filed: Sep. 5, 1997

Related U.S. Application Data

[63] Continuation-in-part of application No. 08/435,128, May 5, 1995, Pat. No. 5,698,677.

[30] Foreign Application Priority Data

Jun. 5, 1994 [DE] Germany ............................ 44 16 166

[51] Int. Cl.⁷ ............................ A61F 38/00; A01N 57/26; A61K 9/127
[52] U.S. Cl. ................................. 514/21; 514/78; 424/450
[58] Field of Search ........................ 514/21, 78; 424/450

[56] References Cited

U.S. PATENT DOCUMENTS

| | | | |
|---|---|---|---|
| 4,241,046 | 12/1980 | Papahadjopoulos et al. | 424/19 |
| 4,348,384 | 9/1982 | Horikosi et al. | 424/101 |
| 4,610,880 | 9/1986 | Giles et al. | 424/101 |
| 4,640,834 | 2/1987 | Eibl et al. | 424/94 |
| 4,721,618 | 1/1988 | Giles et al. | 424/101 |
| 4,937,324 | 6/1990 | Fujikawa et al. | 530/397 |
| 5,198,349 | 3/1993 | Kaufman | 435/69.6 |
| 5,206,023 | 4/1993 | Hunziker | 424/423 |
| 5,225,537 | 7/1993 | Foster | 530/380 |
| 5,354,682 | 10/1994 | Kingdon et al. | 435/214 |
| 5,368,858 | 11/1994 | Hunziker | 424/423 |
| 5,418,130 | 5/1995 | Platz et al. | 435/2 |
| 5,698,677 | 12/1997 | Eibl et al. | 530/381 |

FOREIGN PATENT DOCUMENTS

| | | | |
|---|---|---|---|
| 0159311B1 | 10/1985 | European Pat. Off. | A61L 2/04 |
| 0214737A1 | 3/1987 | European Pat. Off. | A61K 35/16 |
| 0506704B1 | 10/1992 | European Pat. Off. | A61K 31/685 |
| 4325872C1 | 8/1994 | European Pat. Off. | A61K 37/02 |
| 0680764A2 | 11/1995 | European Pat. Off. | A61K 38/48 |
| 368883 | 11/1982 | Germany | A61K 37/02 |
| 2085729A | 10/1980 | United Kingdom | A61K 35/14 |
| 2129685A | 11/1983 | United Kingdom | A61K 31/66 |
| WO90/03808 | 4/1990 | WIPO | A61L 07/00 |
| WO91/02532 | 3/1991 | WIPO | A61K 35/16 |
| WO93/23074 | 11/1993 | WIPO | A61K 37/547 |
| WO95/04524 | 2/1995 | WIPO | A61K 9/127 |

OTHER PUBLICATIONS

Bajaj et al. J. of Biol. Chem., vol. 248, No. 22, pp. 7729–7741 (1973).
Barenholz et al. Biochemistry 16: 2806–2810 (1977).
Barrowcliffe Medline Abstract 94229366 (1993).
Batzri et al. Biochimica et Biophysica Acta 298: 1015–1019 (1973).
Bloom et al. Biochemistry 18(20): 4419–25 (1979).
Brummelhuis Methods of Plasma Protein Fractionation, pp. 117–125, Acad. Press (1980).
Burri et al. Biochimica et Biophysica Acta 923: 176–86 (1987).
Duffy et al. J. of Biological Chemistry 267(24): 17006–17011 (1992).
Giles et al. Blood 59(2): 401–407 (1982).
Hope et al. Biochimica et Biophysica Acta 812: 55–65 (1985).
Juliano et al. Lipsome Technology, 2nd Ed., vol. III, 15–25 (1993).
Lindhout et al. Biochemistry 21: 5494–5502 (1982).
Olson et al. Biochimica et Biophysica Acta 557: 9–23 (1979).
Papahadjopoulos Liposome Technology, 2nd ed., vol. III, pp. 2–13 (1993).
Szoka et al. Proc. Natl. Acad. Sci. USA 75(9): 4194–4198 (1978).
Teng et al. Thombosis Research 22: 213–220 (1981).
Tidrick et al. Surgery 14: 191–196 (1943).
Weiner et al. Journal of Drug Targeting 2: 405–410 (1994).
Zumbuehl et al. Biochimica et Biophysica Acta 640: 252–262 (1981).
Raiz etal, Pharm Dosage Forms; Dipense System 2: 567–602 ch 16, Lieberman et al ed; Marcel Dekker NY, 1988.
Siekmann, "Clinical Experience with Thrombin as an Hemostatic Agen" *Surgery* 14:191–196 (1943).
Riaz et al., Pharmaceutical Dosage Forms: Dispense Systems 2:567–603 (1988), Ch 16 Marcel Dekker, New York, Lieberman et al Ed.
Giles et al., "A Canine Model of Himophilic (Factor VIII:C Deficiency) Bleeding" *Blood* 60:727–730 (1982).

*Primary Examiner*—Russell Travers
*Attorney, Agent, or Firm*—Foley & Lardner

[57] ABSTRACT

The invention relates to a stable preparation which comprises a protein, such as thrombin, that is bound in and/or on (i.e., to) lipid vesicles and that was treated for the inactivation of potentially present viruses. Further, the invention relates to methods for the production of a stable preparation for the treatment of blood coagulation disorders, wherein a protein is bound in and/or on lipid vesicles, and the method comprises a step in which the protein lipid complex is subjected to a treatment for the inactivation of potentially present viruses.

27 Claims, No Drawings

STABLE PREPARATION FOR THE TREATMENT OF BLOOD COAGULATION DISORDERS

The present application is continuation-in-part of application Ser. No. 08/435,128, filed May 5, 1995, U.S. Pat. No. 5,698,677, which is hereby incorporated by reference.

The invention relates to a stable preparation which comprises a protein bound to a phospholipid vesicle, wherein the preparation is subjected to a method for virus inactivation. The invention encompasses biotechnology inventions, including biotechnology products and processes.

BACKGROUND OF THE INVENTION

Coagulation active proteins are considered suitable for the treatment of blood coagulation disorders. In other contexts, such proteins can be used to make antibodies for a variety of uses.

Turning to the coagulation disorders themselves, such disorders are found where the coagulation time deviates from the standard value due to the lack of a coagulation component. The disorders can be inherited as well as acquired through disease conditions.

Hemophilia A is one of the most frequently occurring inherited coagulation disorders. Patients with hemophilia A are prone to frequent hemorrhages as a result of a lack of Factor VIII which can be treated with Factor VIII concentrates. However, in about 15% of the patients Factor VIII neutralizing antibodies, so-called inhibitors, occur, which greatly limits the usefulness of Factor VIII concentrates.

For the treatment of hemophilia A inhibitor patients, complex mixtures of coagulation factors have been employed. The activated prothrombin complex FEIBA® (Immuno) has a "factor eight inhibitor bypassing activity".

In lieu of Factor VIII concentrates, it has been attempted to treat hemophilia A with a mixture of coagulation factor Xa and phospholipids. In U.S. Pat. No. 4,610,880, the treatment of hemophilic dogs with a mixture of Factor Xa and phospholipid vesicles is described. This mixture was not stable, and therefore a Factor Xa-containing solution and a suspension of phospholipid vesicles had to be freshly mixed immediately prior to use. It is stressed that the mixture ratio must be selected in such a way that hemostasis is achieved without causing thromboses.

It is known that combined administration of phospholipid vesicles with Factor Xa, wherein the vesicles and Factor Xa are not bound to one another, increases the danger of thrombosis. On the basis of an in vivo stasis model with rabbits in Blood 59, 401–407 (1982), the increased thrombogenicity of Factor Xa is described when it was tested together with synthetic phospholipids (phosphatidyl choline/phosphatidyl serine lipid vesicles, PCPS vesicles). The danger of thrombosis after administration of prothrombin complex concentrates also is attributed to the combination of coagulation active phospholipids and activated coagulation factors.

It is known from U.S. Pat. No. 4,348,384 to incorporate the coagulation factors Factor VIII and IX inside liposomes. Therewith, a preparation which can be orally or intestinally administered for the treatment of Hemophilia A or B is made available. Here, the liposomes have a size of 1 $\mu$m and protect the Factor VIII or Factor IX from a premature digestion. The administration of these preparations holds no danger of thrombosis because it does not occur intravenously.

The instability of activated coagulation factors in storage is known. A. method is known from *Thrombosis Research* 22: 213–20 (1981) which permits an as stable as possible beta-Factor Xa preparation to be obtained. According to this method, beta-Factor Xa is stored refrigerated in 50% glycerin at pH 7.2 in 0.03 M imidazole buffer. However, a further conversion to inactive fragments also occurs in this method even at 4° C. In a similar manner, the instability of Factor Xa in stabilizing glycerol-water mixtures also is described in *J. Biol. Chem.* 248: 7729–41 (1973).

The combined administration of Factor Xa with liposomes as separate entities also is know. See Giles et al., U.S. Pat. No. 4,721,618. Giles explains that the mixing must be done immediately prior to administration. See Giles at column 5, lines 7–9. Prior to mixing, Giles stores Factor Xa in a 50% glycerol solution at −20° C. See column 4, lines 41–42. The phospholipid vesicles are stored at 4° C. See Giles at column 4, line 62 to column 5, line 3. Giles thus does not disclose binding Factor Xa to a lipid vesicle in order to from a storage-stable preparation.

SUMMARY OF THE INVENTION

The object of the invention is to make available a stable preparation for the treatment of blood coagulation disorders comprising a coagulation active protein.

A further object of the invention is to make available a stable preparation which comprises a protein and is subjected to a treatment for inactivation of potentially-contaminating viruses and the like.

The above objects, and others, are accomplished according to the invention through a stable preparation comprising a complex of suitable proteins and lipids in vesicular form. It has been demonstrated that the stability of an activated coagulation factor is increased in an unexpected manner through the association of an activated coagulation factor, such as Factor Xa, with a phospholipid in vesicular form through the binding in and/or on (i.e., to) a lipid vesicle. Thus the protein is bound to the vesicle. The present invention possesses exceptionally good storage stability in solution, frozen form and lyophilized form. It can even be demonstrated that an activated coagulation factor is protected from physical inactivation such as for example in a lyophilization process or in a treatment for the purpose of virus inactivation. The in vivo activity of the activated coagulation factor also is maintained, which is a measure for the stability of the preparation.

Also provided herein are preparations comprising a protein with clotting activity (such as thrombin) bound to phospholipid-vesicles. These preparations can be used for topical administration, as well as other administration routes.

There is provided, in accordance with one aspect of the invention, a storage-stable preparation comprising thrombin, wherein at least one thrombin molecule is bound to at least one lipidvesicle. The preparation can be treated (for example, heat treatment) to inactivate viruses. The thrombin molecule can be bound to the lipid vesicle by a process selected from the group consisting of hydration, co-lyophilization, co-extrusion, dialysis and sonication. The vesicles can be any size, usually about 30 nm to about 900 nm, and can include or be phospholipids.

The thrombin preparation can be a pharmaceutical preparation, and can be formulated for topical use or parenteral administration. The preparation can include or not include stabilizers. The preparation can be frozen or lyophilized.

There also is provided, in accordance with another aspect of to invention, methods of producing a storage-stable preparation comprising thrombin, wherein at least one thrombin molecule is bound to at least one lipid vesicle, comprising contacting thrombin molecules with a lipid vesicle dispersion or a lipid containing solution, and binding the thrombin molecules to lipid vesicles, including phospholipid vesicles. The binding can be performed by a process selected from the group consisting of hydration, co-lyophilization, co-extrusion, dialysis and sonication. The methods can further comprise inactivating any contaminating viruses in the preparation. The inactivating can employ heat treatment. Other appropriate physical, chemical and physicochemical inactivation methods, such as irradiation and/or filtration, also can be employed. Preferably, the inactivating decreases the thrombin activity by no more than 10%.

The invention also pertains to a storage-stable, virus safe preparation comprising a coagulation protein that is bound to at least one lipid vesicle by a process selected from the group consisting of hydration, co-lyophilization, co-extrusion, dialysis and sonication, wherein the preparation has been treated to inactivate viruses, by procedures such a heat treatment.

The coagulation protein or lipoprotein can be a blood factor involved in the intrinsic coagulation pathway or the extrinsic coagulation pathway, such as an activated coagulation factor or cofactor, and can include enzymes and enzyme inhibitors. Suitable blood coagulation proteins include vitamin K dependent proteins. For example, a coagulation factor, complex or blood protein/lipoprotein can be any one of Factor II, Factor IIa, Factor V, Factor Va, Factor VII, Factor VIIa, Factor VIII, Factor VIII complex, Factor VIIIa, Factor IX, Factor IXa, Factor X, Factor Xa, Factor Xaβ, von Willebrand factor, protein C, activated protein C, protein S, protein Z, tissue factor, Lp(a), and FEIBA or any combinations and/or active fragments of the above factors/proteins/complexes.

The lipid vesicle can be a phospholipid vesicle. Typically, the lipid vesicles have a size of about 30 nm to about 900 nm, but can be smaller or larger than the diameters of this range. Larger vesicle diameters are usually obtained by employing multilamellar vesicles.

The preparations according to the invention can include stabilizers, or can be free of a stabilizer presence. The preparation can be in solution, can be frozen or can be lyophilized.

The present invention also includes for making storage-stable, virus safe preparation comprising a coagulation protein bound to at least one lipid vesicle, comprising: (a) contacting a coagulation protein with a lipid vesicle dispersion to bind the coagulation protein to at least one phospholipid vesicle by a process selected from the group consisting of hydration, co-lyophilization, co-extrusion, dialysis and sonication, thereby yielding lipid-bound protein; and (b) subjecting the lipid-bound protein to virus inactivation procedures to yield said storage-stable, virus safe preparation comprising coagulation protein bound to at least one lipid vesicle.

Other methods include: (a) hydrating a phospholipid film with a coagulation protein-containing solution to form lipid vesicles and bind the coagulation protein to at least one lipid vesicle, thereby yielding lipid-bound protein; and (b) subjecting the lipid-bound protein to virus inactivation procedures to yield said storage-stable, virus safe preparation comprising coagulation protein bound to at least one lipid vesicle.

Preferably, the viral inactivation methods decrease the biological activity of the bound protein by no more than about 10%.

DETAILED DESCRIPTION OF THE INVENTION

Due to the unexpectedly high stability of the preparations according to the invention, it is possible to subject a protein, for example a blood factor of intrinsic and/or extrinsic coagulation pathways respectively and/or a cofactor and/or an inhibitor of blood coagulation and/or a coagulation active lipoprotein, such as for example Lp(a), or an antigen, especially a viral antigen, in the form bound in or on lipid vesicles to a treatment for virus inactivation, preferably a chemical, physical and/or physicochemical treatment and especially a heat treatment. Thereby, the biological activity and/or antigenicity is largely maintained. A preparation according to the invention includes preparation that are virus-safe, which means that any potentially-contaminating viruses have been inactivated and/or removed (partitioned) by the procedures according to the invention.

A preparation according to the invention is considered stable when at least about 40% of the activity of the protein is retained, preferably more than 50%, even when measures such as the lyophilization and reconstitution in the absence of customary stabilizers in unbuffered solution occurs. Stable preparations also are those where at least about 40% of the activity of the active protein, preferably more than 50% and even more preferably more than 60%, is retained by the storage of an aqueous solution of the preparation in the absence of customary stabilizers at 22° C. after 20 hours. Accordingly, a preparation that is storage-stable need not be freshly-prepared immediately prior to administration.

The term "coagulation active protein" or "coagulation protein" are involved in the various coagulation pathways, and include (i) activated or non-activated blood factors of the intrinsic and/or extrinsic coagulation pathways, (ii) coagulation cofactors, and (iii) coagulation active lipoproteins (or coagulation lipoproteins). Coagulation active lipoproteins include lipoproteins that typically interfere with blood coagulation, and include proteins like Lp(a). See Edelberg et al., *Fibrinolysis* 5: 135–43 (1991).

The advantage of an antigen in a preparation according to the invention is above all that, simultaneously with an increased stability of the preparation, the lipid components have an adjuvant effect. Thereby, the preparation according to the invention is especially suitable as an immunizing agent. The antigen can be a recombinant protein and/or polypeptide recombinantly produced. Nevertheless, depending on the type of the cell culture, a contamination with infectious agents can occur. A preparation according to one aspect of the invention, can nonetheless be made virus-safe in view of teachings contained herein.

As determined by the exceptionally high stability, which was also established in vivo after infusion of the preparation of the invention, the preparation is exceptionally suitable for the treatment of patients, especially for the treatment of blood coagulation disorders.

Based upon its structure, a complex of a thrombocytic coagulation active substance, i.e. for example a blood coagulation factor that is naturally present in thrombocytes, is suitable according to the invention as a thrombocyte substitute alone or in combination with further coagulation active substances (which can be referred to a 'coagulation substances') and a lipid vesicle, and, therewith, for the treatment of blood coagulation disorders which are connected with a lack of activated thrombocytes. The structure of the complex is characterized by a protein and a lipid component.

The complex according to the invention imitates the form of a blood platelet, for another functional similarities can be established, such as for example aggregation capability in a protein solution or in the presence of calcium ions or the adsorption on structural proteins of the collagen type. Therefore, the preparation according to the invention can fulfill functions of thrombocytes.

An in vitro test for the determination of the coagulation time of hemophilia A inhibitor plasma serves for the assessment of the effectiveness of the preparation according to the invention for the treatment of hemophilia A inhibitor patients. An effective preparation shortens the coagulation time by at least and preferably to the coagulation time of normal plasma.

It has been surprisingly demonstrated that, through the association of coagulation factor Xa and phospholipid vesicles, the production of a preparation can be obtained that has good storage stability and a high half-life in a Factor VIII inhibitor plasma. A preparation according to the invention is preferably stored in lyophilized form. The lyophilized preparation can be reconstituted to a solution which comprises the complex in vesicular structure. An addition of carbohydrates such as mono- or disaccharide, approximately in an amount of 3–20% (w/w) is advantageous. The stability of the complex according to the invention is further increased in the presence of small amounts of calcium ions. It has been further demonstrated that the complex of coagulation factors and lipid vesicles is not thrombogenic in the pharmaceutical preparations for the treatment of coagulation disorders.

As an active component, a preparation according to the invention comprises a vitamin K dependent protein, for example a factor selected from the group of Factors IIa, VIIA, IXa and Xa, including Factor Xaβ. Furthermore, additional proteins can be included, such as for example the Factors II, VII, IX, X, protein C, activated protein C, protein S and protein Z. It has emerged that the combination of Factor Xa with at least one of the named proteins is particularly effective. An additional amount of Factor VIII, activated Factor VIII, vWF, Factor V and/or activated Factor V is advantageous.

A further embodiment of the preparation according to the invention comprises a complex of an activated blood coagulation factor and lipid vesicles and additionally "tissue factor" or fragments of "tissue factor". Tissue factor protein and active fragments thereof participate in the extrinsic pathway of coagulation. See PCT WO 93/23074.

The proteins included in the complex are preferably human and isolated from a plasma fraction or of recombinant origin. Based on a potential infectiousness, a treatment for the inactivation of infectious agents, such as for example viruses or prions, is appropriate. It is recommended to undertake a heat treatment of the substances or the complex of the proteins and lipid vesicles. The treatment can ensue for example according to EP 0 159 311.

According to a preferred embodiment, a complex of a highly purified Factor Xa (at least 100 U/mg protein), which is free of infectious agents by a treatment for virus inactivation, with phospholipid vesicles is made available.

Based on its stability, the preparation can be made available as a liquid preparation without anything further, i.e. without addition of the commonly used stabilizers such as carbohydrates (saccharose) or protease inhibitors (aprotinin).

However, the preparation can in addition also be stored in liquid deep-frozen form (i.e., that which is normally a liquid is frozen to a solid) or in lyophilized form wherein a polysaccharide amount is advantageous in water removal.

According to the invention, phospholipids in vesicular form can be used as lipid vesicles. The phospholipids can be synthetic or of natural origin. Thereby, a standardized mixture of chemically pure phospholipids is advantageous.

The lipid vesicles can be prepared in various ways such as by sonication of phospholipid dispersions (Barenholz et al., *Biochemistry* 16: 2806–10 (1977); Gregoriades et al., *FEBS Lett.* 14: 95–99 (1971)), the reversed phase evaporation technique (F. Szoka and D. Paphadjopoulos, *Proc. Nat'l Acad. Sci. USA* 75: 4194–98 (1978)), the ethanol injection method (S. Batzri and E. D. Korn, *Biochem. Biophys. Acta* 298: 1015–19 (1973)) or also the removal of detergents from mixed micelles by dialysis methods (O. Zumbuehl and H. G. Weder, *Biochem. Biophys. Acta* 640: 252–62 (1981)). Furthermore, the extrusion method according to Olson et al., *Biochem. Biophys. Acta* 557: 9–23 (1979) also can be used. A dispersion of multilamellar vesicles is prepared by hydration of a lipid film which can be obtained preferably by evaporation of solutions of the lipids in organic solvents with the aid of a rotary evaporator or the like. This dispersion can be subsequently pressed through two stacked polycarbonate filters with nitrogen pressure.

This method should be carried out at a temperature at which the phospholipids are found in a liquid-crystalline state (at least 5° C., preferably at least 10° C. above the phase transition temperature, $T_M$). Optionally, a repeated freeze-thaw cycle is introduced before the extrusion (M. J. Hope et al., *Biochem. Biophys. Acta* 812: 55–65 (1985)). Furthermore, an embodiment has proven to be particularly advantageous. Here, the dispersion of multilamellar vesicles is produced as outlined above, lyophilized, and reconstituted again with water. Thereby, the subsequent extrusion can be carried out particularly easily and also with very high lipid concentrations (for example, 100 mg lipid/ml).

For the production of a complex according to the invention, the described lyophilization step can be carried out after mixing of the vesicle dispersion with the protein, such as coagulation factor Xa. After reconstitution, the complex according to the invention can be further extruded. Another approach for the production of the complex according to the invention is the mixing of the components in the presence of a tenside and the subsequent removal of the tenside, for example by dialysis. A direct hydration of the lipid film with a solution of proteins is also particularly advantageous, wherein optionally lyophilization and reconstitution can be done, whereby the extrusion is made easier. Optionally, in the last variation, the additional lyophilization step can be dispensed with. A direct mixing of the prepared vesicles with the protein in the presence of charged particles or under conditions which permit the incorporation of the protein in and on (i.e., to) the lipid vesicles (concentration, selection of proteins with hydrophobic properties, etc.) also can be done.

For the extrusion process, particularly filters with a diameter of about 30 to about 1000 nm can be used. The typical size of the lipid vesicles (determined by the method of dynamic light scattering) is in the order of about 30 to about 900 nm, preferably about 100 nm to about 500 nm.

The stability of the produced complex is improved when charged particles, for example calcium ions, preferably 1–10 mM, are present. Based on the binding of the coagulation proteins in and on (i.e., to) the lipid vesicles, a purification and isolation of the complex per se is possible. This can occur by gel filtration or ultracentrifugation.

The glycerophospholipids phosphatidyl serine, phosphatidic acid, phosphatidyl glycerol, diphosphatidyl glycerol (cardiolipin) and also phosphatidyl ethanolamine which can exhibit a negative charge are among the suitable phospholipids and are used preferably alone or also combined in a mixture with neutral phospholipids such as phosphatidyl choline and sphingomyelin, wherein the binding by addition of calcium ions is favored. As anionic components, the use of other lipids, such as for example sulfatides or also dicetylphosphate1, phosphatidyl methanol, phosphatidyl-β-lactate and oleic acid is also possible. However, the exclusive use of neutral phospholipids such as phosphatidyl choline or sphingomyelin is also conceivable. However, substances obtained through chemical modification such as the lipid derivatives of the polyethylene glycols or substances from the classes of lysophospholipids or glycolipids are also usable. The use of lipids which can exhibit a positive charge, such as for example stearylamine, dimethyl-dioctadecyl ammonium bromide (DDAB), or also cationic lipids of the type of the 1,2-diacyl-3-trimethyl ammonium propanes (TAP) or the 1,2-diacyl-3-dimethyl ammonium propanes (DAP) also is possible.

A preferred embodiment comprises the use of lipids with anti-viral effect, for example alkylphospholipids (see EP 0 506 704 B1).

In sum, the binding of the protein to the vesicle can be done by any one of: (a) hydration of a phospholipid film with a solution containing the coagulation protein; (b) at least one of co-lyophilization, co-extrusion or sonication of a solution containing the phospholipid vesicle and the coagulation protein; (c) contacting the phospholipid vesicle and the coagulation protein with a tenside and then dialyzing to remove the tenside; (d) mixing the coagulation protein and the phospholipid vesicle in the presence of charged particles; and any combinations thereof.

For stabilization, the phospholipid vesicles can comprise up to 80 Mol % cholesterol as an additional component. All specified lipids can also be used as a sole component, optionally with addition of cholesterol.

For the formation of the complex the lipid vesicles can be found in the gel state or in the liquid-crystalline state, however, the use of systems in the liquid-crystalline state is generally more favorable. In one embodiment of the invention, lipid vesicles comprised of 1,2,-dioleoyl-sn-glycero-3-phosphocholine and 1-palmitoyl-2-oleoyl-sn-glycero-3-phosphoserine are used (for example in a ratio of PC/PS=80/20 (w/w), see Example 1) which are liquid-crystalline at room temperature. The use of phospholipids with unsaturated side chains can, however, lead to a reduced stability by virtue of oxidation. Therefore, for the chemical stability of the vesicles, the use of lipids with fatty acid groups such as those of myristic acid, palmitic acid (Examples 2 and 3) or stearic acid, which are however normally found in the gel state, is preferable. The use of these lipids has been proven as particularly advantageous, however, in mixtures with cholesterol.

The invention is further described by the following examples, which are illustrative of the invention but do not limit the invention in any manner.

Production of Phospholipid Vesicles

EXAMPLE 1

Production of Multilamellar Vesicles

In a 100 ml flask, 40.0 mg 1,2-dioleoyl-sn-glycero-3-phosphocholine and 10.0 mg 1-palmitoyl-2-oleoyl-sn-glycero-3-phosphoserine (Avanti Polar Lipids) are dissolved in 5 ml chloroform and evaporated with the aid of a rotary evaporator under reduced pressure and a temperature of 30° C. After complete removal of the solvent, a vacuum was still held over 30 min at 30 mbar and subsequently dried over a time period of six hours in high-vacuum at 0.1 mbar. The phospholipid film was subsequently hydrated by addition of 5 ml of buffer (20 mM Tris, 150 mM NaCl, pH 7.4) and gentle shaking over one hour at room temperature.

EXAMPLE 2

After formation of a dispersion of multilamellar vesicles according to Example 1, the vesicles were extruded 10 times with $N_2$ pressure through two stacked 100 nm polycarbonate filters laid on top of each other (10 ml thermobarrel extruder, Lipex Biomembranes Inc., Vancouver, Canada). The determination of the particle size of the vesicles produced in this way with the aid of dynamic light scattering (Malvern Zetasizer 4) resulted in a average diameter of about 100 nm.

EXAMPLE 3

From 35.0 mg 1,2-dimyristoyl-sn-glycero-3-phosphocholine (Nattermann Phospholipid GmbH) and 15.0 mg 1,2-dimyristoyl-sn-glycero-3-phosphoserine (Avanti Polar Lipids) in 5 ml chloroform/methanol mixture (2:1, v/v), a phospholipid film was produced as described in Example 1. After addition of 5 ml of buffer (20 mM Tris, 150 mM NaCl, pH 7.4), the film was hydrated at 50° C. by using a rotary evaporator and extruded at 50° C. as described in Example 2.

EXAMPLE 4

From a mixture of 35.0 mg 1,2-dipalmitoyl-sn-glycero-3-phosphocholine (Nattermann Phospholipid GmbH) and 15.0 mg 1,2-dimyristoyl-sn-glycero-3-phosphoserine (Avanti Polar Lipids), phospholipid vesicles were produced as described in Example 3. The hydration of the film and the extrusion also occurred at 50° C.

EXAMPLE 5

From a mixture of 40.0 mg 1,2-dioleoyl-sn-glyceric-3-phosphocholine (Sigma) and 10.0 mg 1,2-dioleoyl-sn-glycero-3-phosphoglycerol or 17.5 mg cardiolipin from bovine heart (Sigma), phospholipid vesicles were produced as described in Examples 1 and 2.

EXAMPLE 6

From a mixture of 40.0 mg 1,2-dioleoyl-sn-glycero-3-phosphocholine and 10.0 mg 1,2-dioleoyl-sn-glyceric-3-phosphate (Sigma), phospholipid vesicles were produced as described in Examples 1 and 2.

EXAMPLE 7

From a mixture of 35.0 mg 1,2-dioleoyl-sn-glycero-3-phosphocholine, 10.0 mg 1-palmitoyl-2-oleoyl-sn-glycero-3-phosphoserine (Avanti Polar Lipids) and 5 mg phosphatidyl inositol from Soya beans (Sigma), phospholipid vesicles were produced as described in Example 1 and 2.

EXAMPLE 8

5 to 80 Mole % cholesterol (Sigma) was added to the mixtures of phosphatidyl choline, phosphatidyl serine, phosphatidyl glycerol, phosphatidic acid and/or phosphatidyl inositol described in Examples 1 to 7 and extruded as described in the respective Examples.

EXAMPLE 9

After hydration of the phospholipid film, the dispersions from Examples 1–8 were shock frozen (liquid $N_2$) and thawed at 37° C. (Examples 2, 5–8) and/or 50° C. (Examples 3 and 4). This process was repeated four times. The multilamellar vesicles produced in this way were extruded as described in the respective Examples. The vesicle preparations resulting therefrom had an average diameter of 100 nm.

EXAMPLE 10

As described in Examples 1–9, multilamellar vesicles were produced through hydration of phospholipid films. The dispersions obtained in this way were frozen at −80° C. and lyophilized. After reconstitution of the lyophilisates with the corresponding volumes of $H_2O$, extrusion was done as described in the respective Examples.

EXAMPLE 11

The production of phospholipid vesicles according to Examples 1–10 was carried out in 150 mM NaCl instead of Tris buffer. The size determination of the vesicles with the aid of dynamic light scattering resulted in a nearly identical size distribution in comparison to vesicles that were produced with buffered solution.

EXAMPLE 12

1,2-dioleoyl-sn-glycero-3-phosphocholine

A mixture of 8.0 mg 1,2-dioleoyl-sn-glycero-3-phosphocholine (Avanti Polar Lipids), 2.0 mg phosphatidyl inositol from Soya beans (Sigma) and 10.0 mg sodium cholate (Sigma) was added in a 50 ml round flask and dissolved in 10 ml of a chloroform/methanol mixture (1:1, v/v). Then, this was evaporated in a rotary evaporator at a bath temperature of 20° C. under reduced pressure until dry, taken up in 10 ml absolute methanol and evaporated again, The film produced in this way was taken up under shaking with 2 ml buffer (20 mM Tris, 150 mM NaCl, pH 7.4). For the production of the vesicles, the clear solution was subsequently dialyzed 24 h against the same buffer at 4° C. The determination of the particle size with the aid of dynamic light scattering resulted in an average diameter of about 70 nm.

Lyophilization of Phospholipid Vesicles in the Presence of Saccharose

EXAMPLE 13

Saccharose to a concentration of 3–20% (w/v) was added to the vesicles produced corresponding to the Examples 1–12. Subsequently, this was frozen at −80° C. and lyophilized. After reconstitution of the lyophilisate, the determination of the size with the aid of dynamic light scattering resulted in an average diameter of about 100 nm. The electron microscopic examination of this solution resulted in a size distribution of about 80 to 130 nm according to visualization with the negative staining method.

Production of a Complex of Factor Xa and Phospholipid Vesicles

EXAMPLE 14

Colyophilization

Factor Xa was produced as follows:

A solution of the prothrombin complex preparation (corresponding to 50,000 U Factor X/l) produced according to the methods of Brummelhuis, METHODS OF PLASMA PROTEIN FRACTIONATION, J. M. Curling (editor), pp 117, Acad. Press., 1980) and heat treated according to the method of EP 0 159 311, was treated in the presence of 12% (v/v) Tween®80 one hour at pH 7.0 and room temperature. Subsequently, this was diluted, mixed with trisodium citrate dehydrate (7.0 g/l), and the proteins of the prothrombin complex precipitated at pH 7.0 by addition of 400 ml 1 M barium chloride solution. The precipitate was washed and resuspended in a 25% (w/v) ammonium sulfate solution containing 50 mM benzamidine HCl. The non-dissolved matter was separated and the solution was brought to 80% saturation with ammonium sulfate in order to precipitate the proteins again. The precipitate was dissolved in buffer and rebuffered chromatogaphically over Sephadexg®-G25 against 25 mM trisodium citrate buffer containing 100 mM NaCl and 1 mM benzamidine HCl, pH 6.0.

The protein containing fractions were further purified by means of a DEAE Sepharose® fast flow column. By increasing the sodium chloride concentration in the citrate buffer (25 mM, pH 6.0), Factor X was eluted separated from the other prothrombin complex proteins. The obtained fraction was rebuffered against 20 mM Tris HCl buffer containing 150 mM sodium chloride and 2 mM calcium chloride (pH 7.4). Subsequently, this was mixed with 0.14 mg RVV (Russel's viper venom, a protease from *Vipera russellii*, Pentapharm) per 100 U FX and stirred one hour at room temperature. The generated Factor Xa was then purified chromatographically with a benzamidine Sepharose® column and concentrated through ammonium sulfate precipitation and subsequently chromatographed over Sephadex®-G25 for the removal of the salt. The produced Factor Xa preparation had a specific activity of at least 100 U Factor Xa/mg protein.

For the production of the complex, a vesicle preparation produced according to the Examples 1–12 was mixed, with or without 2.5 mM calcium chloride, to the Factor Xa fraction. The solution was lyophilized.

After reconstitution, the effectiveness of the preparation in the FEIBA test (test description see AT 350 726) was tested. As a comparison for this, the FEIBA activity of the non-complexed Factor Xa was determined. Before the lyophilization, the FEIBA activity amounted to 1700 U/ml in both cases. After the lyophilization and reconstitution, 1650 U/ml was recovered in the case of the Factor Xa/PCPS complex. The loss of FEIBA activity was much larger in the case of non-complexed Factor Xa. Only 1220 U/ml was recovered.

EXAMPLE 15

Extrusion of a Colyophilisate

A colyophilisate produced according to Example 14 comprising 1000 U Factor Xa as well as 50.0 mg of a phospholipid preparation produced according to Example 6 of 40.0 mg 1,2-dioleoyl-sn-glycero-3-phosphocholine and 10.0 mg 1,2-dioleoyl-sn-glycero-3-phosphate was taken up with water in the original volume and extruded twice at a temperature of 20° C. through two stacked 400 nm polycarbonate filters (Lipex Biomembranes, Inc.). The determination of the particle size with the aid of dynamic light scattering (Malvern Zetasizer 4) resulted in an average diameter of about 450 nm.

EXAMPLE 16

Coextrusion

As described in Example 1, a film was produced from a phospholipid mixture. This was hydrated with a Factor Xa containing solution from Example 14 with or without 2.5 mM calcium chloride. After hydration of the film, it was proceeded as in the Examples 2, 9 and 10 and extruded. Thereby, Factor Xa was complexed with phospholipid vesicles. Saccharose in a concentration of 3–20% (w/v) could be added to the complex produced in this way in order to subsequently lyophilize.

Production of a Complex of Activated Protein C, Factor Xa and Phospholipid Vesicles

EXAMPLE 17

A film was prepared as described in Example 1 from a phospholipid mixture. This was hydrated with the Factor Xa containing fraction from Example 14 as well as with activated protein C in a 20 mM Tris HCl buffer containing 150 mM NaCl and 5 mM $CaCl_2$, pH 7.4. The mixture containing 10 U FXa/ml, 10 U APC/ml and 10 mg phospholipid/ml was lyophilized.

Purification of the Complex of Factor Xa and PCPS Vesicles

EXAMPLE 18

A preparation containing Factor Xa and PCPS vesicles was produced according to the method described in the Examples 14 or 16, wherein saccharose in a final concentration of 5% (w/v) was added to the Factor Xa phospholipid preparation. The lyophilisate was dissolved in water in such a way that the prepared solution contained 2.4 U Factor Xa/ml and 1 mg/ml PCPS vesicles. A column packed with SUPEROSE 6 HR 10/30 (highly cross-linked agarose), Pharmacia, was equilibrated with a buffer (20 mM Tris HCl containing 150 mM NaCl, 0.1% albumin, 0.01% TWEEN 20 (polyoxyethylene sorbitan monolaurate), 1 mM $CaCl_2$, pH 7.4). 500 µl of the PCPS vesicles and Factor Xa containing preparation were chromatographed over the column with a flow rate of 0.4 ml/minute.

In the eluate stream, the UV absorption at 254 nm was measured. The fraction of the exclusion volume containing a complex of PCPS vesicles and Factor Xa was collected.

EXAMPLE 19

A lyophilisate produced according to Example 14 was reconstituted with water such that the finished solution contained 5 U Factor Xa and 5 mg PCPS per ml. 0.5 ml of this solution were mixed with 1 ml of a 30% (w/v) ficoll 400 solution (Pharmacia, in 150 mM sodium chloride solution). This mixture was placed in an ultracentrifugation tube and overlaid with 3 ml of 10% ficoll solution. Finally, this was overlaid with 150 ml NaCl solution and subsequently centrifuged by use of a swing out rotor for 30 minutes at 100,000 g and room temperature.

The layer containing the purified Factor Xa/PCPS complex with lower density than the aqueous solution could be separated as a supernatant.

EXAMPLE 20

A complex comprising activated protein C, Factor Xa and phospholipid vesicles was produced according to Example 17. The lyophilized complex was reconstituted with water and concentrated to a third of the starting volume by centrifugation over ultrafree-MC filter units, exclusion limit 100,000 Daltons (polysulphone membranes, Millipore), 30 minutes at 4000 rpm. The retained material obtained in this way contained the purified complex of activated protein C, Factor Xa and phospholipid vesicles.

Stability of the Complex of Protein and Phospholipids

EXAMPLE 21

Stability of a Factor Xa/PCPS Vesicle Complex in the Lyophilization Process

PCPS vesicles were produced as described in Examples 1 and 2. These were subsequently mixed with Factor Xa, which was produced as described in Example 14, such that the preparation comprised 0.5 mg phospholipid vesicles per ml and 47 U Factor Xa in an aqueous solution of 150 mM/l NaCl and 5 mM/l $CaCl_2$. The complex was lyophilized. As a comparison for this, Factor Xa was lyophilized in the same concentration, however without PCPS vesicles. Subsequently, according to German patent application P4325872.7, the Factor Xa activity was determined in the lyophilized preparations after reconstitution with distilled water in the starting volumes and compared with the Factor Xa amount before the lyophilization (see Table below).

|  | Factor Xa activity (%) | |
| --- | --- | --- |
|  | before lyo | after lyo |
| PCPS/FXa-complex | 100 | 51 |
| Factor Xa | 100 | 20 |

The Table shows the stabilizing influence of vesicular phospholipid on Factor Xa in the copreparation.

EXAMPLE 22

Stability of a Factor Xa/PCPS Vesicle Complex in Solution

A complex of PCPS vesicles and Factor Xa was produced as described in Example 21 and lyophilized. After the reconstitution, the solution was stored at 22° C. over 20 hours. Subsequently, the activity of Factor Xa was determined. The following Table shows the stability of Factor Xa in the PCPS vesicle complex in comparison to non-complexed Factor Xa.

|  | Factor Xa activity (%) | |
| --- | --- | --- |
|  | 0 h | 20 h |
| PCPS/ FXa-complex | 100 | 67 |
| Factor Xa | 100 | 34 |

EXAMPLE 23

Stability of a Protein C/Factor Xa/PCPS Vesicle Complex in the Lyophilization

A complex comprising protein C, Factor Xa and PCPS vesicles was produced analogously to Example 17 and lyophilized. The preparation contained 0.5 mg phospholipid vesicles/ml, 10 U protein C/ml and 47 U Factor Xa/ml in an aqueous solution of 150 mM NaCl. As a comparison for this, protein C and Factor Xa was lyophilized at the same concentrations, however, without PCPS vesicles.

Subsequently, the Factor Xa activity was determined as in Example 21 and the protein C activity was determined by use of a chromogenic test (Immunochrom PC, Immuno) in the lyophilized preparations after reconstitution with distilled water in the starting volumes and compared with the respective amount of Factor Xa and protein C before the lyophilization (see Table).

|  | protein C activity (%) | | Factor Xa activity (%) | |
| --- | --- | --- | --- | --- |
|  | before lyo | after lyo | before lyo | after lyo |
| PCPS/protein C/FXa complex | 100 | 89 | 100 | 84 |
| protein C | 100 | 41 | — | — |
| Factor Xa | — | — | 100 | 23 |

The Table shows the stabilizing influence of phospholipid vesicles on protein C and Factor Xa in the complex.

EXAMPLE 24

Stability of a Protein C/FXa/PCPS Vesicle Complex in Solution

A complex of protein C, Factor Xa and PCPS vesicles and Factor Xa was produced as described in Example 23 and lyophilized. After the reconstitution, the solution was stored at 22° C. over 20 hours. Subsequently, the activity of protein C and Factor Xa was determined. The following Table shows the increased stability of protein C and Factor Xa in the PCPS vesicle complex in comparison to the non-complexed factors.

|  | protein C activity (%) | | Factor Xa activity (%) | |
| --- | --- | --- | --- | --- |
|  | 0 h | 20 h | before lyo | after lyo |
| PCPS/protein C/FXa complex | 100 | 100 | 100 | 88 |
| protein C | 100 | 65 | — | — |
| Factor Xa | — | — | 100 | 9 |

In Vitro Characterization of the Protein/Phospholipid Complexes

EXAMPLE 25

For the testing of the effectiveness of the preparation according to the invention, the following test system was used.

100 μl of FVIII inhibitor plasma (45 Bethesda Units/ml) were mixed in a coagulometer tube with 100 μl 20 mM Tris HCl buffer containing 150 mM NaCl, pH 7.4 (TBS) and recalcified with a further 100 μl of a 0.025 M calcium chloride solution. Immediately after addition of the sample to be analyzed (100 μl), the coagulation time of the mixture was determined by use of a coagulometer (Schnitger/Gross) at 37° C.

When pure TBS buffer was employed as a sample in the represented test substance, the coagulation time amounted to 820 seconds. In comparison to this, the coagulation time of normal plasma in this test system was about 350 seconds.

A preparation produced according to Example 16 was tested at a concentration of 0.88 mU Factor Xa and 0.3 μg phospholipid/ml. As an additive, either 0.1 U FEIBA produced according to the method of AT 368 883 or 0.1 U recombinant Factor VIIA (Novo Nordisk) were tested. Also, a mixture of the FEIBA preparation (0.01; 0.1; 1.0 U/ml) or of Factor X (0.01; 0.1; 1.0 U/ml) produced according to the method from Example 14 with 0.3 pg/ml phospholipid vesicles produced according to the method from Example 1 and 2 were tested. The influence of the tested substances on the coagulation time is given in the following Table.

Shortening of the coagulation time by a preparation containing the complex of coagulation protein and phospholipid vesicles.

| test substance | concentration (mU/ml) | | | | coagulation time (s) |
| --- | --- | --- | --- | --- | --- |
|  | FXa | FEIBA | FVIIa | FX |  |
| Factor Xa/PCPS | 0.88 | — | — | — | 125 |
| Factor Xa/FEIBA/PCPS | 0.88 | 100 | — | — | 82 |
| Factor Xa/Factor VIIa/PCPS | 0.88 | — | 100 | — | 131 |
| FEIBA/PCPS | — | 10 | — | — | 409 |
|  |  | 100 |  |  | 167 |
|  |  | 1000 |  |  | 120 |
| Factor X/PCPS | — | — | — | 10 | 814 |
|  |  |  |  | 100 | 425 |
|  |  |  |  | 1000 | 336 |

Biological In Vitro Activity of Various Phospholipid Vesicle Types

EXAMPLES 26

Phospholipid vesicles comprising mixtures of various phospholipid types in different composition were produced as described in the Examples and processed to copreparations with Factor Xa. The FXa phospholipid vesicle complex resulting therefrom was examined as described in Example 25 on the coagulation shortening effect of FVIII inhibitor plasma. The results (coagulation times) are in the following Table:

| vesicle type | composition w/w % | conc./ml in test substance | | coagulation time (s) |
| --- | --- | --- | --- | --- |
|  |  | mU FXA | μg lipid |  |
| DOPC | 80 | 1.375 | 6.25 | 62 |
| POPS | 20 |  |  |  |
| DOPC | 70 | 1.375 | 6.25 | 65 |
| POPS | 20 |  |  |  |
| CHOL | 10 |  |  |  |
| DOPC | 60 | 1.375 | 6.25 | 57 |
| POPS | 20 |  |  |  |
| CHOL | 20 |  |  |  |
| DOPC | 50 | 1.375 | 6.25 | 56 |
| POPS | 20 |  |  |  |
| CHOL | 30 |  |  |  |
| DOPC | 40 | 1.375 | 6.25 | 69 |
| POPS | 20 |  |  |  |
| CHOL | 40 |  |  |  |
| DOPC | 30 | 1.375 | 6.25 | 58 |
| POPS | 20 |  |  |  |
| CHOL | 50 |  |  |  |
| POPS | 95 | 1.375 | 6.25 | 73 |
| PI | 5 |  |  |  |
| POPS | 90 | 1.375 | 6.25 | 77 |
| PI | 10 |  |  |  |
| POPS | 80 | 1.375 | 6.25 | 71 |
| PI | 20 |  |  |  |
| DOPC | 80 | 1.375 | 6.25 | 135 |
| PI | 20 |  |  |  |

-continued

| vesicle type | composition w/w % | conc./ml in test substance | | coagulation time (s) |
|---|---|---|---|---|
| | | mU FX | ag lipid | |
| DOPC | 80 | 1.375 | 6.25 | 66 |
| POPS | 15 | | | |
| PI | 5 | | | |
| DOPC | 80 | 1.375 | 6.25 | 89 |
| POPS | 10 | | | |
| PI | 10 | | | |
| DOPC | 80 | 1.375 | 6.25 | 110 |
| POPS | 5 | | | |
| PI | 15 | | | |
| DOPC | 75 | 1.375 | 6.25 | 75 |
| POPS | 20 | | | |
| PI | 5 | | | |
| DOPC | 70 | 1.375 | 6.25 | 80 |
| POPS | 20 | | | |
| PI | 10 | | | |
| DOPC | 60 | 1.375 | 6.25 | 72 |
| POPS | 20 | | | |
| PI | 20 | | | |
| DOPC | 50 | 1.375 | 6.25 | 85 |
| POPS | 10 | | | |
| PI | 10 | | | |
| CHOL | 20 | | | |
| DOPC | 50 | 1.375 | 6.25 | 82 |
| POPS | 20 | | | |
| PI | 10 | | | |
| CHOL | 10 | | | |
| CLP | 100 | 1.16 | 5.63 | 76 |
| DOPC | 70 | 1.16 | 6.88 | 69 |
| CLP | 30 | | | |
| DMPC | 70 | 1.16 | 8.45 | 91 |
| DMPS | 30 | | | |
| DPPC | 70 | 1.16 | 8.45 | 123 |
| DMPS | 30 | | | |
| DMPC | 50 | 1.16 | 8.45 | 86 |
| DMPS | 30 | | | |
| CHOL | 20 | | | |
| DMPC | 30 | 1.16 | 8.45 | 67 |
| DMPS | 30 | | | |
| CHOL | 40 | | | |
| DPPC | 50 | 1.16 | 8.45 | 100 |
| DMPS | 30 | | | |
| CHOL | 20 | | | |
| DPPC | 30 | 1.16 | 8.45 | 154 |
| DMPS | 30 | | | |
| CHOL | 40 | | | |
| DOPG | 80 | 1.25 | 10 | 77 |
| DOPC | 20 | | | |
| DOPA | 80 | 1.25 | 10 | 67 |
| DOPC | 20 | | | |
| background | | 0 | 0 | 820 |

Legend:
DOPC = 1,2-dioleoyl-sn-glcero-3-phosphocholine
POPS = 1-palmitoyl-2-olecyl-sn-glycero-3-phosphoserine
CHOL = cholesterol
CLP = diphosphatidyl giycerin (cardiolipin)
PI = phosphatidyl inositol
DMPC = 1,2-dimyristoyl-sn-glycero-3-phosphocholine
DMPS = 1,2-dimyristoyl-sn-glycero-3-phosphoserine
DPPC = 1,2-dipalmitoyl-sn-glycero-3-phosphocholine
DOPG = 1,2-dioleoyl-sn-glycero-3-phosphoglycerin
DOPA = 1,2-dioleoyl-sn-glycero-3-phosphonc acid

EXAMPLE 27

The effectiveness of a complex produced according to Example 14 with 20 mU Factor Xa and 4.96 μg PCPS/ml, and various dilutions thereof, in Factor VIII inhibitor plasma was determined in the following coagulation test immediately after mixing and after an hour incubation at 37° C.

200 μl of sample were mixed in a coagulometer tube with 100 μl 20 mM Tris HCl buffer containing 150 mM NaCl, pH 7.4 (TBS) and recalcified with a further 100 μl of a 0.025 M calcium chloride solution. Immediately after addition of this solution, the coagulation time of the mixture was measured by use of a coagulometer (Schnitger/Gross) at 37° C.

When a 1+1 mixture of FVIII inhibitor plasma (45 Bethesda Units/ml) and TBS buffer was employed as a sample in the represented test substance, the coagulation time amounted to more than 500 seconds.

As a comparison, pure Factor Xa produced according to the method from Example 14 was tested. The results are summarized in the following Table.

Coagulation time of Factor Xa/PCPS and Factor Xa before and after incubation with Factor VIII inhibitor plasma.

| | coagulation time (s) | | | |
|---|---|---|---|---|
| dilution of the | Factor Xa | | Factor Xa/PCPS | |
| stock solution | 0 h | 1 h | 0 h | 1 h |
| undiluted | 77 | 161 | 35 | 69 |
| 1:2 | 95 | 236 | 48 | 111 |
| 1:4 | 117 | 349 | 65 | 185 |
| 1:8 | 152 | >500 | 88 | 314 |
| 1:16 | 224 | >500 | 145 | 400 |
| 1:32 | 314 | >500 | 200 | >500 |
| 1:64 | 441 | >500 | 296 | >500 |
| 1:128 | >500 | >500 | 402 | >500 |

The complex of Factor Xa/PCPS according to the invention has a higher stability than non-complexed Factor Xa. In low concentrations, Factor Xa/PCPS also leads to a shortening of the coagulation time after one hour incubation in Factor VIII inhibitor plasma, whereas non-complexed Factor Xa had already lost its coagulation time shortening activity.

In Vivo Characterization of the Protein/Phospholipid Complexes

EXAMPLE 28

Test on Thrombogenicity

A FEIBA preparation produced according to the method of AT 368 883 was tested for thrombogenicity as a complex with PCPS vesicles and in non-complexed form in the Wessler-Stasis model. The PCPS vesicles were produced according to the method from Example 1 and 2, wherein vesicles of average sizes of 100 nm and/or 50 nm were obtained through a suitable filter choice. 4 U FEIBA and 60 μg PCPS were used per kg rabbit. The thrombogenicity of the FEIBA preparation was not increased by the complex formation with PCPS vesicles. In all cases, no thrombi formation was registered in the stasis model (score=0–1).

Heat Treatment of the Protein/Phospholipid Vesicle Complexes

EXAMPLE 29

Heat Treatment of a Complex of Factor Xa and PCPS Vesicles

A lyophilisate of Factor Xa and PCPS produced according to Example 14 or 16 was treated according to the method of EP 159 311 for 10 hours at 60° C. and 1 hour at 80° C. The Factor Xa activity of the reconstituted solution amounted to more than 90% of the activity before the heat treatment. With the aid of the method of dynamic light scattering (Malvern Zetasizer 4) the preservation of the vesicular structure could be detected.

EXAMPLE 30

Heat Treatment of a Complex of FEIBA and PCPS Vesicles

A complex of phospholipid vesicles and FEIBA was produced analogously to Example 14 and lyophilized. After reconstitution, the lyophilisate contained 30 U FEIBA/ml and 3.4 mg PCPS/ml in a buffer of 4 g Na$_3$citrate.2H$_2$O/l and 8 g NaCl/l, pH 7.0. A lyophilisate corresponding to this composition was treated according to the method of EP 159 311 for 10 hours at 60° C. and 1 hour at 80° C. The FEIBA activity in the reconstituted solution after heat treatment amounted to more than 90% of the activity before the heat treatment With the aid of the method of dynamic light scattering (Malvern Zetasizer 4) the preservation of the vesicular structure could be detected.

EXAMPLE 31

Thrombin (Factor IIa) Bound to Phospholipid Vesicles

The use of a preparation comprising a protein with clotting activity (such as thrombin) and phospholipid-vesicles for topical purposes represents an additional field of application. Parenteral administration of such preparations also should be possible because there are indications of that the preparations may not possess deleterious thrombogenic activity.

Topical application of thrombin alone has been known for many years (Tidrick et al., *Surgery* 14: 191–96 (1943). Although the topical use of liposomes generally has recently become more important (Weiner, et al., *J. Drug Targeting* 2: 405–410 (1994)), no one in the art has bound thrombin to phospholipid vesicles for topical administration purposes. As disclosed herein, systems comprised of multilamellar vesicles, usually offering a diameter of more than about 1000 nm up to about 100 μm, can be used.

The penetration of the protein into the skin is facilitated by use of a liposomal thrombin formulation. Appropriate applications include the use of the preparation in solution, suspension, as ointment or as wound support. The preparation can be treated for the inactivation of viruses, for example, according to EP 159 311.

There are a variety of methods for binding thrombin to a phospholipid vesicle. For example, one procedure for preparing a thrombin/phospholipid-vesicle preparation entails the following:

(I) 250 mg of a phospholipid-mixture of 50 mole % 1,2-Dipalmitoyl-sn-glycero-3-phosphocholin (Nattermann Phospholipid GmbH, Cologne, FRG), 20 mole % 1,2-Dipalmitoyl-sn-glycero-3-phosphoglycerol (Lipoid, Ludwigshafen FRG) and 30 mole % cholesterol (Sigma C-3137) were dissolved in 10 ml chloroform/methanol-mixture (2:1/v:v) in a 100-ml round flask.

(II) A phospholipid film was prepared by evaporating the solvent under reduced pressure and a temperature of 37° C. by use of a rotary evaporator. The film was then hydrated with 10 ml TBS-buffer (20 mM Tris, 150 mM NaCl, pH 7.4) at 50° C. This solution was frozen at −80° C. and lyophilized. The lyophilized powder was then reconstituted with 10 ml H$_2$O and extruded ten times through two stacked polycarbonate filters (pore size about 100 nm) at a temperature of 50° C. (50 ml-thermobarrel-extruder, Lipex Biomembranes Inc., Vancouver Canada). The size of the vesicles prepared by this procedure was determined by dynamic light scattering (Zetasizer 4, Malvern Instruments, Worcestershire, UK) and yielded a diameter of about 100 nm.

(III) The vesicle-preparation was diluted with TBS-buffer to a concentration of 5 mg phospholipid/ml and mixed (1:1/v:v) with a solution of bovine thrombin (Pentex®, Miles Inc., USA) in TBS-buffer (1000 U thrombin/ml). The preparation was frozen at −80° C. and lyophilized. After lyophilization and reconstitution with the appropriate volume of water, an average diameter of 3100 nm was determined by means of dynamic light scattering. Subsequently, the vesicles were extruded two times through two stacked 400 nm-filters. After the extrusion an average vesicle size of 260 nm was measured (Malvern Zetasizer 4).

(IV) In order to separate free thrombin from the preparation, the preparation was centrifuged at 35000× g, the supernatant decanted and the pellet resuspended with TBS-buffer. The centrifugation procedure was repeated twice. The thrombin/phospholipid-vesicle complex was characterized by means of a chromogenic substrate test (substrate Th-1, Immuno Vienna) and by means of the method of thrombin clotting time (J ürgens, *Dtsch. Arch. Klin. Med.* 200: 67 (1952). Immediately after preparation, a thrombin activity of 1.0 IU/ml (chromogenic substrate) was determined. No acceleration of clot formation was observed with this sample in comparison to a buffer control by use of a test system for the determination of thrombin clotting time in a normal plasma.

As a means for quantifying the amount of bound thrombin, vesicles were subjected by detergent treatment to destroy the vesicles. Vesicle samples are incubated with 5% Triton-X 100 for 20 min at 37° C. 35 IU Thrombin/ml were indicated by use of the chromogenic substrate test, 30 IU/ml by means of the thrombin clotting time method.

The thrombin-vesicle preparation was then mixed with saccharose to a final concentration of 5% (w/v), frozen at −80° C. and lyophilized. The lyophilized product was treated 10 hours at 60° C. and 1 hour at 80° C. according to the procedure of EP 159 311. The total activity of thrombin of the reconstituted solution amounted to more than 90% of the activity before heat treatment. Via dynamic light scattering techniques (Malvern Zetasizer 4), the preservation of the vesicular structure after reconstitution was demonstrated.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein.

What is claimed is:

1. A storage-stable vesicular preparation comprising thrombin, wherein at least one thrombin molecule is bound to at least one lipid vesicle, and wherein the preparation is treated to inactivate viruses.

2. A preparation according to claim 1, wherein the preparation is heat-treated to inactivate viruses.

3. A preparation according to claim 1, wherein the thrombin molecule is bound to the lipid vesicle by a process selected from the group consisting of hydration, co-lyophilization, co-extrusion, dialysis and sonication.

4. A preparation according to claim 1, wherein the lipid vesicle is a phospholipid vesicle.

5. A preparation according to claim 1, wherein the lipid vesicle has a size of about 30 nm to about 900 nm.

6. A method of producing a storage-stable preparation comprising thrombin, wherein at least one thrombin molecule is bound to at least one lipid vesicle, comprising:

contacting thrombin molecules with a lipid vesicle dispersion or a lipid containing solution, and binding the thrombin molecules to lipid vesicles.

7. A method according to claim 6, wherein the binding is performed by a process selected from the group consisting of hydration, co-lyophilization, co-extrusion, dialysis and sonication.

8. A method according to claim 6, further comprising inactivating any contaminating viruses in the preparation.

9. A method according to claim 8, wherein the inactivating decreases the thrombin activity by no more than 10%.

10. A method according to claim 6, wherein the lipid vesicle is a phospholipid vesicle.

11. A storage-stable preparation comprising lipid vesicles with thrombin molecules bound thereto.

12. A preparation according to claim 11, wherein the preparation is treated to inactivate viruses.

13. A preparation according to claim 12, wherein the preparation is heat-treated to inactivate viruses.

14. A preparation according to claim 11, wherein thrombin is bound to lipid vesicles by a process selected from the group consisting of hydration, co-lyophilization, co-extrusion, dialysis and sonication.

15. A preparation according to claim 11, wherein the preparation is a pharmaceutical preparation.

16. A preparation according to claim 15, wherein the preparation is formulated for topical use.

17. A preparation according to claim 15, wherein the preparation is formulated for parenteral administration.

18. A preparation according to claim 11, wherein the lipid vesicles are phospholipid vesicle.

19. A preparation according to claim 11, wherein the lipid vesicles have a size of about 30 nm to about 900 nm.

20. A preparation according to claim 11, wherein the preparation does not include stabilizers.

21. A preparation according to claim 11, wherein the preparation is frozen.

22. A preparation according to claim 11, wherein the preparation is lyophilized.

23. A method of producing a storage-stable comprising lipid vesicles with thrombin molecules bound thereto, comprising:

contacting thrombin molecules with a lipid vesicle dispersion or a lipid containing solution, and binding the thrombin molecules to lipid vesicles to obtain lipid vesicles with thrombin bound thereto.

24. A method according to claim 22, wherein the binding is performed by a process selected from the group consisting of hydration, co-lyophilization, co-extrusion, dialysis and sonication.

25. A method according to claim 23, further comprising treating the lipid vesicles with thrombin bound thereto in order to inactivate contaminating viruses.

26. A method according to claim 25, wherein the treating decreases the thrombin activity by no more than 10%.

27. A method according to claim 23, wherein the lipid vesicle is a phospholipid vesicle.

* * * * *

UNITED STATES PATENT AND TRADEMARK OFFICE
CERTIFICATE OF CORRECTION

PATENT NO. : 6,017,891
DATED : January 25, 2000
INVENTOR(S) : Johann EIBL, et al..

It is certified that error appears in the above-identified patent and that said Letters Patent is hereby corrected as shown below:

On the title page, item [30], Foreign Application Priority Data, delete "Jun. 5, 1994" and replace with --May 6, 1994--.

Signed and Sealed this

Eighth Day of May, 2001

Attest:

NICHOLAS P. GODICI

Attesting Officer       Acting Director of the United States Patent and Trademark Office